United States Patent [19]

Muccigrosso et al.

[11] Patent Number: 4,612,402
[45] Date of Patent: Sep. 16, 1986

[54] OXIDATION OF OLEFINS USING RHODIUM NITRO COMPLEX

[75] Inventors: Deborah A. Muccigrosso, Somerville; Frank Mares, Whippany; Steven E. Diamond, New Providence; Jeffrey P. Solar, Flanders, all of N.J.

[73] Assignee: Allied Corporation, Morris Township, Morris County, N.J.

[21] Appl. No.: 362,725

[22] Filed: Mar. 29, 1982

[51] Int. Cl.$^4$ .............................................. C07C 45/28
[52] U.S. Cl. .................... 568/408; 568/398.8; 568/365; 568/309; 568/426; 568/469.9; 568/475; 556/136
[58] Field of Search ............ 568/360, 401, 408, 398.8, 568/305, 309, 426, 469.9, 475; 260/465 D, 465.4

[56] References Cited

U.S. PATENT DOCUMENTS 4,104,312  8/1978  Angstadt et al. .................... 568/342
4,322,562  3/1982  Tovrog et al. ....................... 568/400

OTHER PUBLICATIONS

Hitchman et al, Coordination Chem. Rev., vol. 42, pp. 55–122 (1982).
Andrews et al, J.A.C.S., vol. 103, pp. 2894–2896 (1981).
B. S. Tovrog et al., J. Am. Chem. Soc., 1980, 102, 6616–6618.

Primary Examiner—James H. Reamer
Attorney, Agent, or Firm—Richard C. Stewart; Gerhard H. Fuchs

[57] ABSTRACT

A process for the oxidation of olefinically unsaturated substrates of the formula R—CH=CH-R' wherein R and R' are independently selected from members of the group consisting of H, alkyl, alkenyl, cycloalkyl, aryl and halo-, cyano- and ether-substituted alkyl, alkenyl, cycloalkyl and aryl which comprises reacting in the liquid phase said substrate with a rhodium nitro complex of the formula $L_nRhNO_2$, wherein n is 4 or 5 and wherein $L_n$ represents any combination of monodentate, bidentate, tridentate and tetradentate ligands such as to provide four or five bonding sites, for a time sufficient to produce an oxidized product of the formula $RCH_2C(O)R'$ and a reduced product of the formula $L_nRhNO$ is disclosed. A preferred embodiment of the process wherein the rhodium nitro complex contains at least one ligand replaceable by olefin to be oxidized and operates to produce the oxidized product $RCH_2C(O)R'$ in the absence of other Group VIII metals as co-catalyst is also disclosed.

11 Claims, No Drawings

OXIDATION OF OLEFINS USING RHODIUM NITRO COMPLEX

BACKGROUND OF THE INVENTION

This invention relates to an oxidation process using rhodium nitro complexes to transfer oxygen to organic substrates having an olefinic bond. More particularly, this invention relates to a liquid phase oxidation process using rhodium nitro complexes, in the absence of other Group VIII metals as activators, to transfer oxygen to organic substrates having an isolated olefinic bond.

Only a few rhodium nitro complexes are known. These known rhodium complexes are either polynitro rhodium complexes or thermally unstable pentammine rhodium mononitro dicationic complexes, e.g., $[(NH_3)_5RhNO_2]^{2+}(Cl^-)_2$ (See for Example, M. A. Hitchman and G. L. Rowbottom, Coordination Chemistry Reviews, 1982,42, 55–122). Further, both types of these known rhodium nitro complexes are not obtainable by oxidation of the corresponding nitrosyl complexes by molecular oxygen and therefore are unsuitable for the oxidation process of the present invention.

U.S. Pat. No. 4,191,696 (B. S. Tovrog et al.) discloses a liquid phase oxidation process wherein nitro complexes of Group VIII metals such as cobalt transfer oxygen to easily oxidizable organic substrates such as triphenylphosphine. However, when the substrate is a more difficultly oxidizable compound such as a compound having an isolated olefinic bond, U.S. Pat. No. 4,191,696 discloses that it is useful to activate the olefinic compound to be oxidized by complexing the olefinic bond with a divalent palladium compound or to activate the metal nitro complex by use of a Lewis acid such as boron trifluoride etherate.

B. S. Tovrog et al. in our U.S. Pat. No. 4,322,562, that is a continuation-in-part of U.S. Pat. No. 4,191,696, discloses a cyclic or catalytic oxidation process wherein a nitro complex of a Group VIII metal such as cobalt transfers an oxygen atom from the nitro ligand to an olefinic compound complexed with a divalent palladium compound. The nitrosyl ligand of the metal nitrosyl complex, formed as a coproduct with the oxidation product of the olefinic compound, is reoxidized by molecular oxygen, in the presence of a monodentate base such as pyridine, to the nitro ligand.

M. A. Andrews et al. in J.A.C.S., Vol. 103, No. 10, 1981, pages 2894–96 disclose the catalytic air oxidation of olefins to ketones by use of a divalent palladium nitro complex, $Pd(CH_3CN)_2ClNO_2$.

SUMMARY OF THE INVENTION

The present invention provides a process for the oxidation of olefinically unsaturated substrates of the formula $R-CH=CHR'$ wherein R and R' are independently selected from members of the group consisting of H, alkyl, alkenyl, cycloalkyl, aryl, and halo-, cyano- and ether-substituted alkyl, alkenyl, cycloalkyl and aryl, which comprises reacting, in the liquid phase, said substrate with a rhodium nitro complex of the formula $L_nRhNO_2$ wherein n is 4 or 5 and wherein $L_n$ represents any combination of monodentate, bidentate, tridentate and tetradentate ligands such as to provide four or five bonding sites; for a time sufficient to produce an oxidized product of the formula $RCH_2C(O)R'$ and a reduced product of the formula $L_nRhNO$.

DETAILED DESCRIPTION OF THE INVENTION

We have discovered that rhodium nitrosyl complexes of the formula $L_nRhNO$ are oxidized by molecular oxygen to the corresponding rhodium nitro complexes of the formula $L_nRhNO_2$ and that oxygen is transferred from the nitro ligand of said rhodium complexes to olefinically unsaturated substrates of the formula $R-CH=CHR'$. This oxygen transfer results in the oxidation of olefinically unsaturated substrates such as ethylene to acetaldehyde, and higher molecular weight alkenes to mixtures of alkanones with the concomitant formation of the rhodium nitrosyl complex. The nitro ligand, $-NO_2$ and the nitrosyl ligand $-NO$ are each bound to the rhodium atom of the complex via the nitrogen atom. While a cyclic or catalytic oxidative transfer process wherein molecular oxygen is employed in the presence of the rhodium nitro or nitrosyl complex and the olefinically unsaturated substrate has not been observed, such a cyclic or catalytic oxygen transfer is deemed possible by appropriate choice of reaction conditions and ligands.

The rhodium nitro complexes found useful in the oxygen transfer process of the present invention have the formula $L_nRhNO_2$ wherein n is 4 or 5 and wherein $L_n$ represents any combination of monodentate, bidentate, tridentate and tetradentate ligands such as to provide four or five bonding sites at rhodium. The preferred rhodium nitro complexes of the present invention contain at least one labile ligand, i.e., replaceable by the olefinically unsaturated substrates to be oxidized. Rhodium nitro complexes found particularly useful are the complexes wherein rhodium is formally $Rh^{+3}$. Other useful complexes have ligands selected from the group consisting of oxygen containing ligands such as tetrahydrofuran (THF), $(CH_2)_4O$, diphenyl ether, 1,2-dimethoxyethane and bis(2-methoxyethyl)ether, halides such as $F^-$, $Cl^-$ and $Br^-$, sulfur containing ligands such as N,N-dialkyldithiocarbamates, e.g., N,N-dimethyldithiocarbamate and weak nitrogen ligands such as aromatic and aliphatic nitriles, such as benzonitrile (PhCN) and acetonitrile ($CH_3CN$) and strong nitrogen ligands such as aromatic amines, e.g., 2,2'-bipyridine, $(C_5H_4N)_2$ or bipy, pyridine, and quinoline.

The ligand may be tetradentate, for example a saloph ligand of the formula $[1,2\text{-}(ortho\text{-}OC_6H_4CH=N)_2C_6H_4]^{-2}$, a porphyrin dianion, i.e., tetraphenylporphyrin$^{2-}$(TPP). Also the ligand may be bis-bidentate such as 2,2'-bipyridine, phthalic acid dinitrile, glutarodinitrile, and the like. The ligands may also be monodentate ligands such as aromatic amines represented by pyridine, quinoline, pyrrole, and other nitrogen heterocycles. Such rhodium nitro complexes can be prepared by the same or similar procedures as used in the prior art, such as described in the experimental section hereinafter.

Of course, ligands such as phosphines, arsines, and isonitriles that interfere with the oxidation process of the present invention are to be avoided.

By the term "weak nitrogen ligand" as used herein, it is meant a nitrogen containing ligand such as aromatic and aliphatic nitriles e.g., benzonitrile and acetonitrile that can be readily displaced from the rhodium nitro complex by olefinically unsaturated substrates in the absence of activators such as other Group VIII metals. Among rhodium(III) nitro complexes found useful to transfer oxygen to olefinically unsaturated substrates are those complexes having ligands selected from the group consisting of oxygen containing ligands, halides, weak nitrogen containing ligands and no more than one monodentate strong nitrogen ligand. Particularly useful rhodium nitro complexes that transfer oxygen to olefinically unsaturated substrates are those containing one to four monodentate, aromatic or aliphatic nitrile ligands, e.g., complexes such as $[(PhCN)_4RhNO_2]^{2+}2X^-$, $[(CH_3CN)_4RhNO_2]^{2+}2X^-$, $[(C_4H_7N)_4RhNO_2]^{2+}2X^-$, $[(CH_3CN)_3RhClNO_2]^+X^-$, $[(PhCN)_3RhClNO_2]^+Xt^-$, where X is an outer sphere monoanion such as $BF_4^-$, $PF_6^-$, or $ClO_4^-$, or $2X^-$ is an outer sphere dianion such as $SO_4^{2-}$; complexes of the formulas $(R_1R_2O)_2RhNONO_2X$, wherein $R_1R_2O$ is an oxygen-containing ligand such as an aliphatic or an aromatic ether, especially a cyclic aliphatic ether such as tetrahydrofuran (THF) and wherein X is halide, especially chloride, such as in $(THF)_2RhNONO_2Cl$, $(Ph_2O)_2RhNONO_2Cl$; and those complexes having no more than one pyridine containing ligand such as $[(CH_3CN)_2(C_5H_5N)RhNO_2Cl]^+X^-$, $[(CH_3CN)_3(C_5H_5N)RhNO_2]^{2+}2X^-$ wherein $X^-$ is the same as defined hereinabove.

In contrast to the behavior of the abovedescribed rhodium nitro complexes that contain at least one labile ligand and that oxidize olefinically unsaturated substrates, especially isolated olefins in the absence of activators or co-catalysts such as Group VIII metals, nitro complexes of other Group VIII metals, such as platinum and iridium which is in the same triad as rhodium, require activation of the olefin to be oxidized by coordination to palladium(II). Nitro complexes of Group VIII metals containing only non-labile ligands such as py(salpoh)$CoNO_2$ or py(TPP)$CoNO_2$ require activation of the olefin to be oxidized by coordination of the olefin to palladium(II).

By the term "strong nitrogen ligand" as used herein, it is meant a nitrogen containing ligand such as pyridine, quinoline, 2,2'-bipyridine, $(C_5H_4N)_2$, Schiff bases such as saloph, porphyrins such as tetraphenylporphyrin (TPP), and the like that are difficult to be displaced from the rhodium nitro complex by olefinically unsaturated substrates. When the rhodium nitro complex contains such strong nitrogen ligands, it is necessary to activate the olefinically unsaturated substrate toward oxygen transfer from the nitro ligand by complexing said substrate with another Group VIII metal such as divalent platinum or divalent palladium. Particularly useful activators are divalent palladium compounds such as bis(benzonitrile)palladium dichloride.

The quantity of activator (such as Group VIII metal complex) used is not critical and can be as much as equimolar with the olefinically unsaturated substance to be complexed, or can be much less or much more.

Among the general characteristics of rhodium nitro complexes useful in the oxidation of isolated olefins in accordance with the present invention are the following:

(1) Oxidation of the corresponding rhodium nitrosyl complex by molecular oxygen to the rhodium nitro complex;

(2) Ease of preparation of the rhodium nitro complex having at least one rhodium bound ligand that is replaceable by the olefin to be oxidized;

(3) Ability to transfer oxygen to isolated olefins in the presence of Group VIII metals other than rhodium, such as palladium(II), Pd(II); and (4) Optionally, the ability to transfer oxygen to isolated olefins to produce oxidized olefins in the absence of other Group VIII metals such as Pd(II).

Prior to discovery of the rhodium nitro complexes of the present invention, there were no known rhodium nitro complexes that were obtainable by oxidation of the corresponding rhodium nitrosyl complexes by molecular oxygen.

While Andrews (JACS 1981, 103, 2896–2897) has shown that known palladium nitro complexes are obtainable by oxidation by molecular oxygen of the palladium nitrosyl complex, no nitro complex of nickel, another Group VIII metal in same triad as palladium, has been found useful in the oxidation of isolated olefins.

During the course of the development of the present invention, it was observed that a cobalt nitro complex failed to oxidize an isolated olefin such as ethylene activated by a divalent platinum compound. The cobalt nitro complex was recovered unchanged and neither ethylene oxide nor acetaldehyde was detected. See Example XVI.

Nitrosyl complexes of iridium, a Group VIII metal in the same triad as rhodium, were prepared. However, in our hands, attempted oxidations of nitrosyl iridium complexes failed to produce a nitro iridium complex. See Examples XVIII and XX.

Olefinically unsaturated substrates found amenable to oxidation by rhodium nitro complexes have the formula R—CH=CHR' wherein R and R' are independently selected from members of the group consisting of H, alkyl, alkenyl, cycloalkyl, aryl, and halo-, cyano- and ether-substituted alkyl, alkenyl, cycloalkyl and aryl. Examplary of the olefinically unsaturated substrates oxidizable in the process of the present invention are compounds having at least one isolated olefinic bond such as alkenes of 2 to 20 carbons, alicyclic compounds of 3 to 20 carbons, alkenyl aromatics such as styrene, 3-phenyl-1-propene, 1-phenyl-1-propene, 1-phenyl-2-butene, and 3-phenylcyclohexene, alkenyl ethers with the double bond separated by at least two carbon atoms from the ether oxygen such as in methyl 4-butenyl ether, bis(phenyl-4-pentenyl) ether, etc., halogenated derivatives of the above examplary compounds, with no halogen in vinylic or allylic positions such as 4-chloro-1-hexene, 1-chloro-3-pentene, 4,4,4-trifluoro1-butene, cyano derivatives of the above examplary compounds containing no allylic cyano group such as $CH_2=CHCN$, 4-pentenonitrile, 3-phenyl-propenonitrile. Particularly useful olefinically unsaturated substances oxidizable in the present invention are terminal olefins having at least one isolated olefinic bond and having the formula $CH_2=CHR''$ wherein R'' is independently selected from group consisting of aryl and straight and branched chain alkyl groups of 1 to 18 carbon atoms. Ethylene, propylene and styrene are more preferred.

The quantity of rhodium nitro complex used in the present invention is not critical and can be as much as equimolar with the olefinically unsaturated complex to be oxidized, or can be much more or much less.

Solvents found useful in the process of the present invention are aprotic solvents such as nitromethane, dimethyl sulfoxide, acetonitrile, and tetrahydrofuran (THF) that are able to dissolve at least a catalytic amount of the rhodium nitro complexes that can be neutral, monocationic or dicationic. Nitromethane is particularly useful in the process of the present invention.

Reaction temperature and time are not critical. Convenient reaction temperatures are 0° to 200° C., preferably 40° to 70° C. Useful reaction times are 0.5 to 24 hrs.

Reaction pressure is not critical. For gaseous olefins, autogeneous pressures are useful.

The following examples are illustrative of our invention and of the best mode we now contemplate for carrying out the invention, but are not to be interpreted as limiting.

GENERAL EXPERIMENTAL PROCEDURES

All reactions were run under an atmosphere of argon unless stated otherwise. Infrared spectra were recorded on a Perkin-Elmer Model 283 spectrophotometer. Gas-Liquid chromotographic (GLC) analyses were performed on a Hewlett-Packard Model 5880 and Model 5830A equipped with a 2.48 m (8 ft)×3.2 mm ($\frac{1}{8}$ inch) Porapak QS column for analysis of the oxidation products of ethylene and propylene and with a 1.83 m (6 ft)×3.2 mm ($\frac{1}{8}$ inch) 5% Carbowax on Suppelcoport for analysis of the oxidation products of 1-octene. The temperature was programmed in the range of 75°–220° C. at a rate of 30°/min. GLC-MS data was recorded on a Finnigan Model 3300; $^1$H-NMR spectra were recorded on a Varian Model T-60 spectrometer.

Starting Materials and Solvents

The rhodium nitrosyl complexes and $(PhCN)_2PdCl_2$ were prepared and purified by published procedures: For $[Rh(NO)_2Cl]_2$ see G. Dolcette et al, *Inorganica Chimica Acta*, 1972, 6, 531; for $[Rh(NO)Cl_2]$ see G. R. Crooks et al. *J. Chem Soc(A)*, 1970; 1662; for $[Rh(CH_3CN)_4NO](BF_4)_2$ see N. G. Connelly et al, *J. Chem Soc., Dalton Trans*, 1977 70; and for [Bipy Rh(CO)$_2$]PF$_6$ see G. Mestroni et al. *J. Organomet. Chem*, 1974, 65, 119. Acetonitrile and dimethyl sulfoxide (DMSO) were dried over 4 Å molecular sieves, then treated with CaH$_2$ and finally vacuum distilled. Nitromethane was dried over CaH$_2$ and vacuum distilled. Ethylene and propylene were dried by passage of each over heat activated 3 Å molecular sieves. Nitrosyl hexafluorophosphate and nitrosyl tetrafluoroborate were purchased from Alfa Ventron and used without further purification.

EXAMPLE I (Bipyridyl)tris(acetonitrile)nitrosylrhodium bis(hexalfluorophosphate) [(bipy)(CH$_3$CN)$_3$RhNO]$^{2+}$(PF$_6^-$)$_2$ (Complex 1)

To a solution of (1,5-cyclooctadiene)chlororhodium dimer, [(1,5-COD)RhCl]$_2$ (4.7 g) in methanol (200 mL), a three fold excess of 2,2'-bipyridyl (4.47 g) was added. The resulting solution was stirred for 3h. Addition of an excess of ammonium hexafluorophosphate (NH$_4$PF$_6$, 4.0 g) resulted in the formation of 1,5-cyclooctadiene)(2,2'-bipyridyl)rhodium hexafluorophosphate [(1,5-COD)(bipy)Rh]$^+$(PF$_6^-$) in a form of a red precipitate (9.50 g, 97% yield) which was filtered and dried in inert atmosphere. Anal: Calcd for C$_{18}$H$_{20}$F$_6$N$_2$PRh: C, 42.20; H, 3.93; N, 5.47. Found: C, 41.85; H, 3.97; N, 5.47.

The above cationic complex (1.0 g) was dissolved in degassed acetonitrile (20 mL) and the resulting solution was cooled to 0° C. Addition of nitrosyl hexafluorophosphate (NOPF$_6$, 96% purity, 0.37 g) resulted in a green solution which was stirred at room temperature for 50 min. Then diethyl ether (50 mL) was added and a green oil separated as a heavier layer. The green oil slowly crystallized. The crystals (1.28 g, 97%) were filtered off, washed with diethyl ether and dried in vacuum. Anal: Calcd for C$_{16}$H$_{17}$F$_{12}$N$_6$P$_2$Rh C, 27.36; H, 2.44; N, 11.97. Found: C, 27.57; H, 2.61; N, 11.49; The IR spectrum in nujol showed a nitrosyl band at 1658 cm$^{-1}$.

The same complex was prepared by the reaction of [(bipy)(CO)$_2$Rh]$^+$PF$_6^-$ with nitrosyl hexafluorophosphate in acetonitrile.

EXAMPLE II (Bipyridyl)tris(acetonitrile)nitrorhodiumbis-(hexafluorophosphate) [(bipy)(CH$_3$CN)$_3$RhNO$_2$]$^{2+}$(PF$_6^-$)$_2$ (Complex 1a).

Oxygen was bubbled through a solution of 1 (0.49 g) in acetonitrile (20 mL) at room temperature for 24 hours. When diethyl ether was added to the solution, a green oil was formed which slowly solidified. The pale green solid (0.438 g) was filtered off, washed with diethyl ether and dried in vacuum. Anal: Calcd for C$_{17}$H$_{17}$F$_{12}$N$_6$P$_2$O$_2$Rh: C, 25.08; H, 2.38; N, 11.70. Found: C, 25.76; H, 2.55; N, 10.28. IR showed no peak in the Rh-NO region (1658-cm$^{-1}$). The Rh-NO$_2$ region at (800 cm$^{-1}$) is obstructed by the broad PF$_6^-$ band.

EXAMPLE III

Tetrakis(acetonitrile)nitrosylrhodiumbis(tetrafluoroborate) [(CH$_3$CN)$_4$RhNO]$^{2+}$ (BF$_4^-$)$_2$ (Complex 2).

(Connelly, N. G.; Draggett, P. T.; Green, M.; Kue, T. A.; J. Chem. Soc. Dalton Trans. 1977, 70.) and dinitrosyl chlororhodium dimer [Rh(NO)$_2$Cl]$_2$ (Complex 3) (Crooks, G. R. Johnson, B. F. G; J. Chem. Soc. A; 1970, 1662) were prepared according to published procedures.

EXAMPLE IV

Tetrakis(Acetonitrile)nitrorhodium bis(tetrafluoroborate) [(CH$_3$CN)$_4$RhNO$_2$]$^{2+}$(BF$_4^-$) (Complex 2a).

A solution of complex 2 (0.2 g), prepared as described in Example III, in acetonitrile (20 mL) was placed in a Fisher-Porter tube and the tube was pressurized to 275 kPa (40 psi) with oxygen. After 24 h of stirring at room temperature, the system was vented and the solvent evaporated. A yellow hydroscopic solid of compound 2a was obtained. Anal: Calcd for C$_8$H$_{12}$B$_2$F$_8$N$_2$O$_2$Rh: C, 19.74; H, 2.49; N, 14.38; Found: C, 20.85; H, 2.78; N, 14.09. The infrared spectrum showed new bands at 815 cm$^{-1}$, 1270 cm$^{-1}$, 1313cm$^{-1}$ and 1380 cm$^{-1}$ typical for the nitro complex, Rh-NO$_2$, and no band in the nitrosyl region.

EXAMPLE V

Tetrahydrofurannitronitrosylchlororhodium, (THF)(NO$_2$)(NO)RhCl (Complex 3a).

A solution of complex 3 (0.3 g) in tetrahydrofuran, THF, (20 mL) was placed into a Fisher-Porter tube and the tube was pressurized to 344 kPa (50 psi) with oxygen. After stirring at room temperature for 66 h, the system was vented and the solution was evaporated to dryness yielding a dark brown solid, Compound 3a. The structure was approximate since more than exactly one THF per Rh is remaining in the complex. The IR spectrum contained two NO bands at about 1713 cm$^{-1}$ and at 1630 cm$^{-1}$ and bands at 868 cm$^{-1}$, 1268 cm$^{-1}$ and 1360cm$^{-1}$ that are characteristic for the nitro ligand.

EXAMPLE VI

Attempted Oxidation of Ethylene by 1a in Absence of a Cocatalyst.

Complex 1a [(bipy)(CH$_3$CN)$_2$RhNO$_2$]$^{2+}$(PF$_6^-$)$_2$ (0.0499 g, 0.0725 mmol) and n-octane, an internal standard for GLC (0.0664 g) were dissolved in acetonitrile (10 mL) saturated with ethylene. The reaction flask was stoppered by a serum cap and heated to 70° C. No formation of acetaldehyde was observed even after 22 h.

EXAMPLE VII

Stoichiometric Oxidation of Ethylene by 1a with (PhCN)PdCl$_2$ as a Co-Catalyst.

Complex 1a (0.058 g. 0.082 mmol) was dissolved in a mixture of 10 mL of solvent containing n-octane (0.1 g), bis(benzonitrile)dichloropalladium (PhCN)$_2$PdCl$_2$ (0.06 g, 0.15 mmol) and saturated in ethylene. The capped flask was heated to 70° C. whereupon formation of acetaldehyde was observed. In 2.5 h, a practically quantitative yield of acetaldehyde (0.085 mmol) was obtained as shown by a GLC-MS analysis.

EXAMPLE VIII

Stoichiometric Oxidation of Ethylene in Absence of a Cocatalyst

Complex 2a [(CH$_3$CN)$_4$RhNO$_2$]$^{+2}$(BF$_4^-$)$_2$ 0.719 g, 0.148 mmol) and n-octane (0.1 g) were dissolved in dry and degassed nitromethane (6 mL). The mixture was placed under argon into a Fisher-Porter tube and the tube was pressurized to 138 kPa (20 psi) with ethylene and heated to 60° C. After 16 h, quantitative yield of acetaldehyde (0.15 mmol) was present in the reaction mixture as determined by GLC.

EXAMPLE IX

Stoichiometric Oxidation of Propylene

Procedure of Example VIII was repeated using 0.29 mmol of [RhNO$_2$NOCl]$_n$, 10 mL of tetrahydrofuran as solvent and propylene at one atmosphere initial pressure at a reaction temperature of 60° C. for 19 hrs. The product was acetone (0.051 mmol) by GLC-MS Analysis.

EXAMPLE X

Oxidation of 1-octene

Complex 1a [(bipy)(CH$_3$CN)$_3$RhNO$_2$]$^{+2}$(PF$_6^-$)$_2$](0.1018 g, 0.14 mmol) and bis(benzonitrile)dichloropalladum (PhCN)$_2$PdCl$_2$ (0.1053 g), 0.275 mmol) were dissolved in a degassed (with Ar) and dry solution of 1-octene (1 mL) and undecane (ca. 0.1 g) in acetonitrile (7 mL). Under argon the mixture was heated to 70° C. and the extent of reaction was followed by GLC. After 22.5 h, 0.17 mmols of a mixture of 2-octanone (0.093 mmol), 3-octanone (0.067 mmol) and 4-octanone (0.029 mmol) were present by GLC-MS Analysis.

EXAMPLE XI

Attempted Catalytic Oxidation of 1-Octene in the Presence of Complex 1a

The same solution as described in Example X was placed into a Fisher-Porter tube. The tube was pressurized to 289 kPa (42 psi) with oxygen and heated to 70° C. After 21.5 h 0.228 mmol (1.6 molar turnovers) of a mixture of 2-octanone and 3-octanone was present in the reaction mixture. Because of the slow oxidation of Complex 1 to 1a, Pd$^{+2}$ in (PhCN)$_2$PdCl$_2$ was reduced to Pd° which precipitated out of the reaction mixture.

EXAMPLE XII

Oxidation of 1-Octene

Complex 2a [(CH$_3$CN)$_4$RhNO$_2$]$^{+2}$(BF$_4^-$)$_2$ (0.0376 g, 0.077 mmol) was dissolved in a dry and degassed (with argon) mixture of 1-octene (1 mL), undecane (ca. 0.1 g) and nitromethane (6 mL). The solution was placed under argon into a Fisher-Porter tube. The tube was pressurized to 220 kPa (32 psi) with argon and heated to 60° C. After 16 h, (0.050 mmol) of the expected 2-octanone was formed. Very small amounts of 3- and 4-octanone were also formed.

EXAMPLE XIII

Attempted Catalytic Oxidation of 1-Octene in the Presence of [(CH$_3$CN)$_4$RhNO$_2$](BF$_4$)$_2$ Complex 2a A dry solution of complex 2a (0.040 g, 0.0822 mmol), 1-octene (1 mL) in nitromethane (6 mL) was pressurized in a Fisher-Porter tube to 349 kPa (50 psi) with oxygen. After 22 h at 60° the reaction was stopped and biphenyl (0.0330 g, 0.214 mmol) was added. 0.117 mmol (1.4 molar turnover) of a mixture of octanones (predominantly 2-octanone) was present in the reaction mixture.

EXAMPLE XIV

Oxidation of 1-Octene

Complex 3a, Rh(NO$_2$)NOCl:THF (0.0485 g, 0.169 mmol) was dissolved in a dry and degassed solution of 1-octene (2.25 mL) in dimethylsulfoxide (9 mL) and the resulting mixture was heated under argon to 60°. After 24 h, 0.0258 mmol of 2-octanone was present in the reaction mixture.

EXAMPLE XV

Attempted Catalytic Oxidation of 1-Octene

The procedure of XIV was followed except that O$_2$ was added. No catalytic oxidation was observed due to the competing rearrangement of [Rh(NO)$_2$Cl]$_n$ to a rhodium chlorohyponitrite, ClRh(—O—N=N—O—), which is inactive.

EXAMPLE XVI

Attempted Oxidation of Ethylene by (py)(TPP)CoNO$_2$ in the presence of Platinum(II) activator A platinum-ethylene complex K[Pt )C$_2$H$_4$)Cl$_3$] (0.0745 g, 0.202 mmol) and the cobalt nitro complex, (py)(TPP)CoNO$_2$ (0.1605 g, 0.201 mmol) were dissolved in tetrahydrofuran (10 mL) which had been thoroughly flushed with argon. This solution was stirred for 1 h. at 55° C. GLC analysis of the reaction mixture did not reveal the presence of either acetaldyehyde or ethylene oxide. After evaporation of the solvent, IR analysis of the resultant solid revealed the presence of the cobalt nitro complex. However, the bands were shifted from their normal positions. No bands attributable to the cobalt nitrosyl complex were present. It is believed that a complex, (py)(TPP)Co—N-(O)—O—CH$_2$—Pt—Cl formed, but failed to produce oxidized product such as ethylene oxide or acetaldehyde.

EXAMPLE XVII

Preparation of [Ir(1,5-COD)(CH$_3$CN)NOCl]$^+$BF$_4^-$ by the Reaction of [Ir(1,5-COD)Cl]$_2$ with NOBF$_4$ The (1,5-Cyclooctadiene)chloroiridium dimer, [Ir(1,5-COD)Cl]$_2$ (0.1088 g, 0.162 mmol) was suspended in degassed acetonitrile (5 mL) at 0° C. The addition of NOBF$_4$ (95%) (0.075 g, 0.61 mmol) resulted in a red-brown solution which was warmed to R.T. and stirred for 1 hour. Addition of Et$_2$O resulted in a red oil which solidified to a red-brown solid on stirring. The IR spectrum contained 2 broad NO bands at 1630 and 1545 cm$^{-1}$.

EXAMPLE VIII

Attempted Oxidation of [Ir(1,5-COD)(CH$_3$CN)NOCl$^-$]BF$_4$

[Ir(C$_8$H$_{12}$)(CH$_3$CN)NOCl]BF$_4$ (0.2 g) was dissolved in acetonitrile (10 mL), placed in a Fisher-Porter tube and pressurized to 344 kPa (50 psi) with oxygen. After 24 hr. of stirring at R.T. the system was vented. Addition of Et$_2$O resulted in a red-brown solid. IR analysis indicated no oxidation of the nitrosyl to the nitro had taken place.

EXAMPLE XIX

Attempted Preparation of nitrosyl Iridium Complex Reaction of [Ir(C$_8$H$_{12}$)$_2$Cl]$_2$ with NOBF$_4$

[Ir(C$_8$H$_{12}$)$_2$Cl]$_2$ (0.6277 g, 0.70 mmol) was suspended in 20 mL degassed acetonitrile and cooled to 0° C. Addition of NOBF$_4$ (0.2048 g, 95%) resulted in a clear solution which was stirred at 0° C. for 30 min. then warmed to RT and stirred for 3 hrs. IR analysis of the complex isolated by volume reduction and trituration with Et$_2$O revealed no NO bands. The proposed structure of the isolated complex is [Ir(CH$_3$CN)$_5$Cl](BF$_4$)$_2$.

EXAMPLE XX

Reaction of [Ir(C$_8$H$_{14}$)$_2$Cl]$_2$ with NOCl and Attempted Oxidation of Nitrosyl Iridium Complex

[Ir(C$_8$H$_{14}$)$_2$Cl]$_2$ (0.34 g, 0.38 mmol) was suspended in 15 mL degassed CH$_3$CN and an excess of NOCl in CH$_2$Cl$_2$ (2.7 mmol) was added dropwise. The resulting deep red solution was stirred for 3 hrs. Addition of Et$_2$O resulted in an oil which slowly crystallized into a reddish-brown solid. IR analysis revealed a Rh-NO band at 1660 cm$^{-1}$ with a shoulder at 1630 cm$^{-1}$. Attempts to oxidize this complex at 344 kPa (50 psi) of oxygen did not result in the isolation of a nitro complex.

We claim:

1. A a process for the oxidation of olefinically unsaturated substrates of the formula R—CH=CH—R' wherein R and R' are independently selected from members of the group consisting of H, alkyl, alkenyl, cycloalkyl, aryl, and halo-, cyano- and ether substituted alkyl, alkenyl, cycloalkyl and aryl, which comprises reacting, in the liquid phase and in the substantial absence of an additional Group VIII metal, said substrate with a rhodium nitro complex of the formula L$_n$RhNO$_2$ wherein n is 4 or 5 and wherein L$_n$ represents any combination of monodentate, bidentate, tridentate and tetradentate ligands such as to provide four or five bonding sites, for a time sufficient to produce an oxidized product of the formula RCH$_2$C(O)R' and a reduced product of the formula L$_n$RhNO.

2. A process for the oxidation of olefinically unsaturated substrates of the formula R—CH=CH—R' wherein R and R' are independently selected from members of the group consisting of H, alkyl, alkenyl, cycloalkyl, aryl, and halo-, cyano-, and ether-substituted alkyl, alkenyl, cycloalkyl, and aryl, which comprises reacting, in the liquid phase and in the absence of an additional group VIII metal said substrate with a rhodium nitro complex of the formula L$_n$RhNO$_2$, wherein n is 4 or 5 and wherein L$_n$ is selected from the group consisting of halids, oxygen-containing ligands, weak nitrogen ligands, and mondentate nitrogen ligands and wherein L$_n$RhNO$_2$ contains no more than one monodentate strong nitrogen ligand, such as to provide four or five bonding sites, for a time sufficient to produce an oxidized product of the formula RCH$_2$C(O)R' and a reduced product of the formula L$_n$RhNO.

3. The process of claim 2 wherein each ligand is a nitrile.

4. The process of claim 3 wherein L$_n$RhNO$_2$ is (CH$_3$CN)$_4$RhNO$_2$.

5. The process of claim 2 wherein L$_n$RhNO$_2$ is [THF]$_2$RhNONO$_2$Cl.

6. The process of claim 2 wherein the olefinically unsaturated substrate is a terminal olefin having at least one isolated olefinic bond and having formula CH$_2$=CHR" wherein R" is independently selected from the group consisting of aryl and straight and branched chain alkyl gorups of 1 to 18 carbon atoms.

7. A process for the oxidation of olefinically unsaturated substrates of the formula R—CH=CH—R' wherein R and R' are independently selected from members of the group consisting of H, alkyl, alkenyl, cycloalkyl, aryl, and halo-, cyano-, and ether-substituted alkyl, alkenyl, cycloalkyl, and aryl, which comprises reacting, in the liquid phase, said substrate with a rhodium nitro complex of the formula L$_n$RhNO$_2$, wherein n is 4 or 5 and wherein L$_n$ is selected from the group consisting of nitriles, halides, cyclic ethers and NO for a time sufficient to produce an oxidized product of the formula RCH$_2$C(O)R' and a reduced product of the formula LhRhNO.

8. A process according to claim 7 wherein Ln is a nitrile.

9. A process according to claim 8 wherein L$_n$RhNO$_2$ is (CH$_3$CN)$_4$RhNO$_2$.

10. A process according to claim 7 wherein L$_n$RhNO$_2$ is [THF]$_2$RhNONO$_2$Cl.

11. A process according to claim 1 wherein L$_n$RhNO$_2$ contains no monodentate strong nitrogen ligands.

* * * * *